(12) United States Patent
Fisher

(10) Patent No.: US 8,230,719 B2
(45) Date of Patent: Jul. 31, 2012

(54) METHOD FOR IDENTIFYING THE COMPOSITION OF A SAMPLE

(75) Inventor: Chad Fisher, Kansas City, MO (US)

(73) Assignee: MRIGlobal, Kansas City, MO (US)

( * ) Notice: Subject to any disclaimer, the term of this patent is extended or adjusted under 35 U.S.C. 154(b) by 73 days.

(21) Appl. No.: 12/767,874

(22) Filed: Apr. 27, 2010

(65) Prior Publication Data

US 2010/0206045 A1    Aug. 19, 2010

Related U.S. Application Data

(63) Continuation of application No. 11/940,684, filed on Nov. 15, 2007, now Pat. No. 7,823,439.

(51) Int. Cl.
*G01N 30/04* (2006.01)

(52) U.S. Cl. .............. 73/23.42; 73/23.36; 73/23.41; 95/82; 95/86; 96/101; 96/103; 96/104

(58) Field of Classification Search .......... 73/23.35, 73/23.36, 23.41, 23.42; 95/82, 86, 87; 96/101, 96/103, 104; 42/89; 422/89
See application file for complete search history.

(56) References Cited

U.S. PATENT DOCUMENTS

| | | | |
|---|---|---|---|
| 3,119,251 A | 1/1964 | Bowers | |
| 3,234,779 A | 2/1966 | Dawson, Jr., | |
| 4,883,504 A | 11/1989 | Gerstel | |
| 5,135,549 A * | 8/1992 | Phillips et al. | 95/8 |
| 5,196,039 A * | 3/1993 | Phillips et al. | 210/656 |
| 5,240,606 A | 8/1993 | Lapidus et al. | |
| 5,492,555 A | 2/1996 | Strunk et al. | |
| 5,846,292 A | 12/1998 | Overton | |
| 6,004,514 A | 12/1999 | Hikosaka et al. | |
| 6,296,771 B1 | 10/2001 | Miroslav | |
| 6,494,078 B1 | 12/2002 | Klee | |
| 6,497,138 B1 | 12/2002 | Abdel-Rahman et al. | |
| 6,730,228 B2 | 5/2004 | Petro et al. | |
| 6,808,635 B2 | 10/2004 | Brann | |

(Continued)

FOREIGN PATENT DOCUMENTS

CN    1261761 C    6/2006

(Continued)

OTHER PUBLICATIONS

Yinliang F. Hsieh, Neal Gordon, Fred Regnier, Noubar Afeyan, Stephen A. Martin, and George J. Vella; Multidimensional chromatography coupled with mass spectrometry for target-based screening, Molecular Diversity, 1996, pp. 189-196, vol. 2, ESCOM Science Publishers B.V.

*Primary Examiner* — Daniel Larkin
(74) *Attorney, Agent, or Firm* — Husch Blackwell LLP

(57) ABSTRACT

The present invention is directed to a method for multidimensional gas chromatography for separating the analytes of a complex sample. The method comprises the steps of introducing the sample onto a first column whereby the sample is separated into at least two segments, introducing at least one segment into a heartcut device whereby the segments are selectively separated into at least two heartcut fractions, introducing at least one of the fractions onto a second column whereby at least one fraction is further separated into at least two analytes, introducing at least one analyte from the second column to a gas chromatography connector, introducing the analyte from the connector to a third column, and introducing the analyte from the third column into a detector whereby the analyte is analyzed and identified.

19 Claims, 3 Drawing Sheets

U.S. PATENT DOCUMENTS

| | | |
|---|---|---|
| 6,855,258 B2 | 2/2005 | Petro et al. |
| 6,923,907 B2 | 8/2005 | Hobbs et al. |
| 6,976,384 B2 | 12/2005 | Hobbs et al. |
| 7,018,540 B2 | 3/2006 | Brann |
| 7,214,320 B1 | 5/2007 | Gregori et al. |
| 7,217,360 B2 | 5/2007 | Brann |
| 7,383,718 B2 | 6/2008 | McCurry et al. |
| 7,490,506 B2 * | 2/2009 | Chaintreau et al. .......... 73/23.41 |
| 2002/0194898 A1 | 12/2002 | Klee |

FOREIGN PATENT DOCUMENTS

| | | |
|---|---|---|
| GB | 850608 | 10/1960 |
| JP | 2006234830 A | 9/2006 |
| WO | 2006078859 A2 | 7/2006 |

* cited by examiner

US 8,230,719 B2

METHOD FOR IDENTIFYING THE COMPOSITION OF A SAMPLE

CROSS-REFERENCE TO RELATED APPLICATIONS

This application is a continuation of and claims priority to the U.S. patent application Ser. No. 11/940,684, filed Nov. 15, 2007 now U.S. Pat. No. 7,823,439 which is hereby incorporated by reference to the extent permitted by law.

STATEMENT REGARDING FEDERALLY SPONSORED RESEARCH OR DEVELOPMENT

None.

BACKGROUND OF THE INVENTION

Gas-liquid chromatography, commonly referred to as gas chromatography or GC, is a process used for analyzing a complex sample by separating the analytes within the sample to determine the identity of the analytes in the sample. Other information about the analytes, such as the concentration of each analyte within the sample, may also be obtained. A gas chromatograph is used for separating the sample by injecting the sample onto a column through which the sample passes. Different chemical analytes of the sample pass in a mobile phase at different rates depending on their various chemical and physical properties and their interaction with a specific column filling, called the stationary phase. During the process of gas chromatography, the analytes of the sample are separated as a consequence of being partitioned between the mobile gaseous phase and the stationary phase held in the column or by passing through a series of columns. The function of the mobile phase is to transport the sample through the column but not to interact with it. The sample's motion through the column is inhibited by the adsorption of the analytes either onto the column walls or onto packing materials within the column. The rate at which the analytes progress along the column depends on the strength of adsorption, which in turn depends on the properties of the analyte. Since each type of analyte has a different rate of progression, the various analytes of the sample are separated as they progress along the column and reach the end of the column at different times. A detector is used to monitor the outlet stream from the column, thus, the time at which each analyte reaches the outlet identifies the analyte and may determine the concentration of that analyte as well.

When a sample is complex and has multiple analytes it may be difficult to separate out and identify a particular analyte of interest. In multidimensional gas chromatography the sample undergoes a series of separation steps. The sample is introduced to at least two columns allowing for a better separation of the analytes. Increasing the separation of the sample increases the accuracy and the precision of the results. Multiple columns and separation steps allow for a more effective separation of the analytes from the sample, but this process does not necessarily target a particular analyte. Therefore, it would be beneficial to have a method that improves the separation of the sample and allows for the targeting of specific analytes.

The equipment used for chromatography can be expensive and, as complex samples progress through the chromatograph, build-up occurs. It would be beneficial to employ a method that keeps the equipment cleaner and reduces the need for maintenance.

SUMMARY OF THE INVENTION

In one of many illustrative, non-limiting aspects of the present invention, there is provided a method for identifying the composition of a sample. The method includes introducing the sample onto a first column whereby the sample is separated into at least two segments, introducing at least two segments to a heartcut device whereby at least two segments are selectively separated into at least two heartcut fractions, introducing at least one of the fractions onto a second column whereby at least one fraction is further separated into at least two analytes, introducing at least one analyte from the second column to a gas chromatography connector, introducing the analyte from the connector to a third column, and introducing at least one analyte from the third column into a detector whereby at least one analyte is analyzed and identified.

In another of many illustrative, non-limiting aspects of the present invention, there is provided a chromatograph for identifying the composition of a sample. The chromatograph includes a first column whereby the sample is separated into at least two segments, a heartcut device whereby the segments are introduced and then selectively separated into at least two heartcut fractions, a second column whereby at least one heartcut fractions are introduced and further separated into at least two analytes, a gas chromatography connector and thermal modulator whereby the analyte is introduced from the second column, a third column whereby at least one analyte is introduced from the connector and modulator, and a detector whereby at least one analyte is introduced from the third column and then analyzed to identify at least one analyte.

BRIEF DESCRIPTION OF THE SEVERAL VIEWS OF THE DRAWING

In the accompanying drawings that form a part of the specification and that are to be read in conjunction therewith.

DETAILED DESCRIPTION OF THE INVENTION

There is provided herein a method for separating analytes of a complex sample and determining information about the analytes. A device for separating analytes of a complex sample is also provided. The method of the present invention is used to improve the separation of analytes from the sample. Improved separation means improved results and better efficiency of the chromatography process. The method also improves the lifetime of the columns and other equipment, reducing the need for maintenance.

Figure 1:
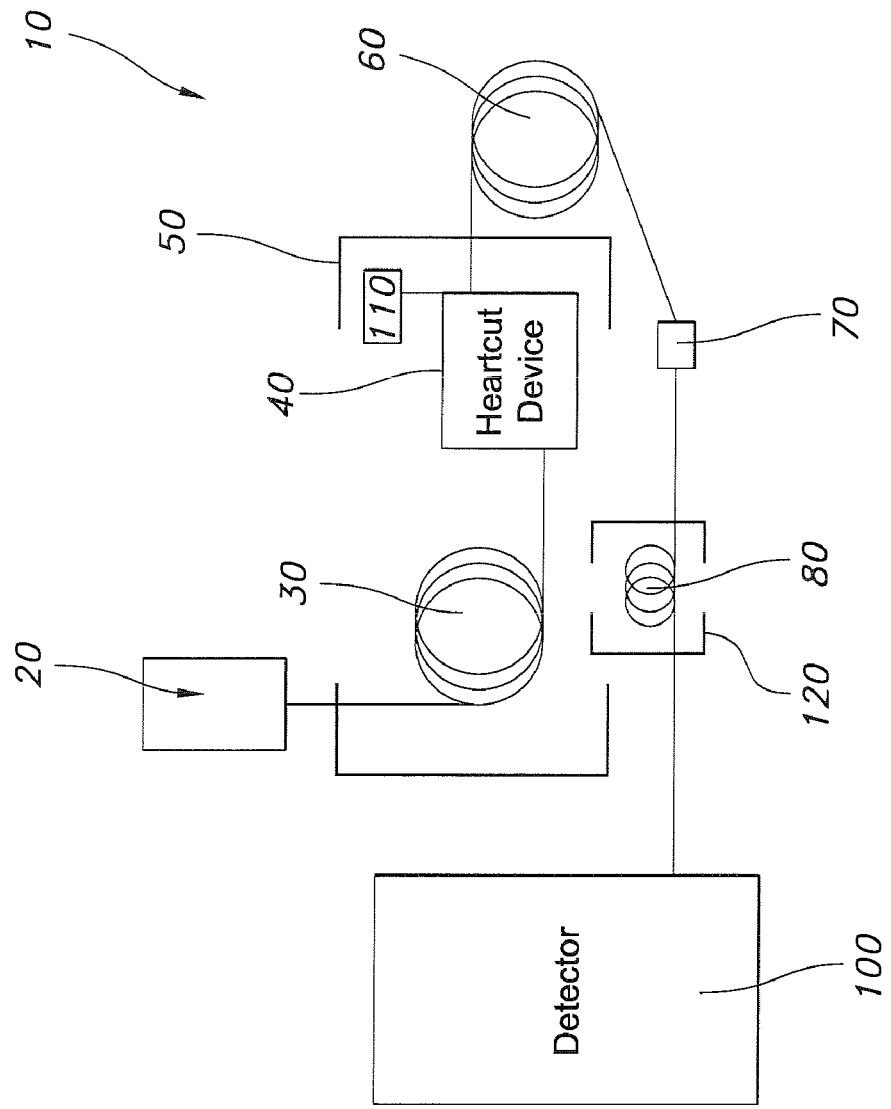
FIG. 1 is a schematic diagram illustrating one embodiment of the method of the present invention.

FIG. 1 illustrates one embodiment of the method of the present invention. The method for separating analytes of a complex sample utilizes a chromatograph 10. Chromatograph 10 includes a sample introduction device 20, a first column 30, a heartcut device 40, a temperature controlling device 50, a second column 60, a connector and modulator 70, a third column 80 and a detector 100. The sample is introduced onto first column 30 by introduction device 20. Introduction device 20 may be, but is not limited to, a split/splitless injector, an on-column inlet, a thermal desorption device, a PTV injector, a gas source inlet, a gas switching valve, a purge-and-trap system, a solid microextraction, or another injection device now known or hereafter developed that is suitable for injecting the sample onto first column 30. First column 30, second column 60, and third column 80 may be, but are not limited to, capillary columns, packed columns, micropacked columns, microfast columns, or any other type of column now known or hereafter developed. In an illustrative example, each column is a capillary column with first column 30 and second column 60 each having a size of about 30 m×0.25 mmID×1 µm df, and third column 80 having a size of about 1 m×0.10 mmID×0.1 µm df. On first column 30, the sample is separated into at least two segments. The segments are introduced into heartcut device 40 and are selectively separated into at least two heartcut fractions. As an added benefit, heartcut device 40 may remove much of the sample's matrix leaving second column 60 and detector 100 cleaner and reducing the need for maintenance. In one embodiment, a SGE heartcut device is heartcut device 40. In an alternate embodiment, a Dean's switch is heartcut device 40. In another alternate embodiment, a Gerstel heartcut device is heartcut device 40. In another alternate embodiment, a valve is heartcut device 40. It will be appreciated by one in the art that alternative devices that allow for the selective separation of fractions from the segments may be used in place of heartcut device 40. In another embodiment, heartcut device 40 is operably connected to a midpoint detector 110 to aid in setting the correct timing for heartcut device 40 to transfer the fractions onto second column 60.

In one embodiment, as illustrated in FIG. 1, first column 30 and heartcut device 40 are located within temperature controlling device 50. In an illustrative example, the temperature within temperature controlling device 50 preferably ranges from about 40° C. to 320° C. Temperature controlling device 50 may be, but is not limited to, an oven, a heating jacket, or other appropriate device for controlling the temperature of the equipment now known or that is hereinafter developed. In one embodiment, second column 60 may also be located within temperature controlling device 50. At least one of the heartcut fractions is then introduced onto second column 60 whereby at least one fraction is further separated into at least two analytes. At least one of the analytes is then introduced to connector 70. Connector 70 may be, but is not limited to, a gas chromatography×gas chromatography modulator that may be either a thermal or valve-based modulator. It will be appreciated by one in the art that the temperature of temperature controlling device 50 may be customized for the target analytes. At least one analyte is then introduced from connector 70 onto third column 80. In one embodiment, third column 80 is within a separate temperature controlling device 120 that allows for a separate temperature control for third column 80. At least one analyte is introduced to detector 100 from third column 80. Detector 100 may be, but is not limited to a mass spectrometer, a thermal conductivity detector, a discharge ionization detector, an electron capture detector, a flame photometric detector, a Hall electrolytic conductivity detector, a helium ionization detector, a nitrogen phosphorus detector, a mass selective detector, a photo-ionization detector, a pulsed discharge ionization detector, and any other detection device that is now known or hereafter developed suitable for analyzing and identifying at least one analyte.

In one embodiment, injection device 20 is operably connected to first column 30 that in turn is operably coupled to heartcut device 40. Heartcut device 40 is operably coupled to second column 60 that in turn is operably coupled to connector 70. Connector 70 is operably coupled to third column 80 that in turn is operably coupled to detector 100. These are in a downstream series with each other.

Figure 2:
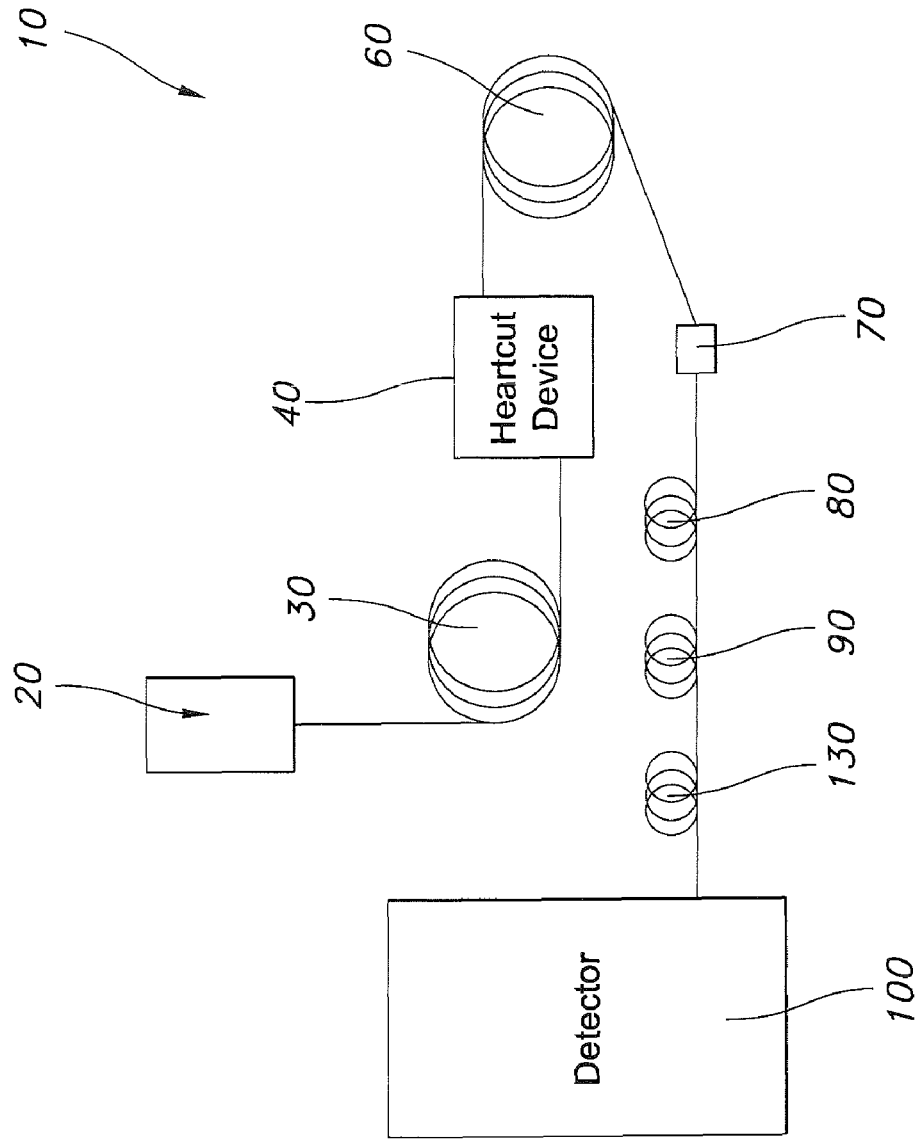
FIG. 2 is a schematic diagram illustrating one embodiment of the method of the present invention.

FIG. 2 illustrates another embodiment of the method of the present invention directed to a method for identifying the composition of a sample using chromatograph 10 as described in a manner hereinabove that further comprises a fourth column 90. At least one analyte is introduced from third column 80 onto fourth column 90. The analyte is then introduced from fourth column 90 to detector 100 for analysis and identification of at least one analyte. In another embodiment, a fifth column 130 is located between fourth column 90 and detector 100.

The method of the present invention may be used to selectively target specific analytes in a sample. Heartcut device 40 aids in selectively targeting analytes for analysis and identification. Targeted analyte analysis has a variety of applications such as it may be used in the agricultural industry for determining the composition of pesticides or used to determine the composition of pollutants. Other industry applications include, but are not limited to, the petroleum industry, the food industry, and the flavoring industry. It will be appreciated by one skilled in the art that the method of the present invention may be used in any situation where current methods of gas chromatography are used.

Figure 3:
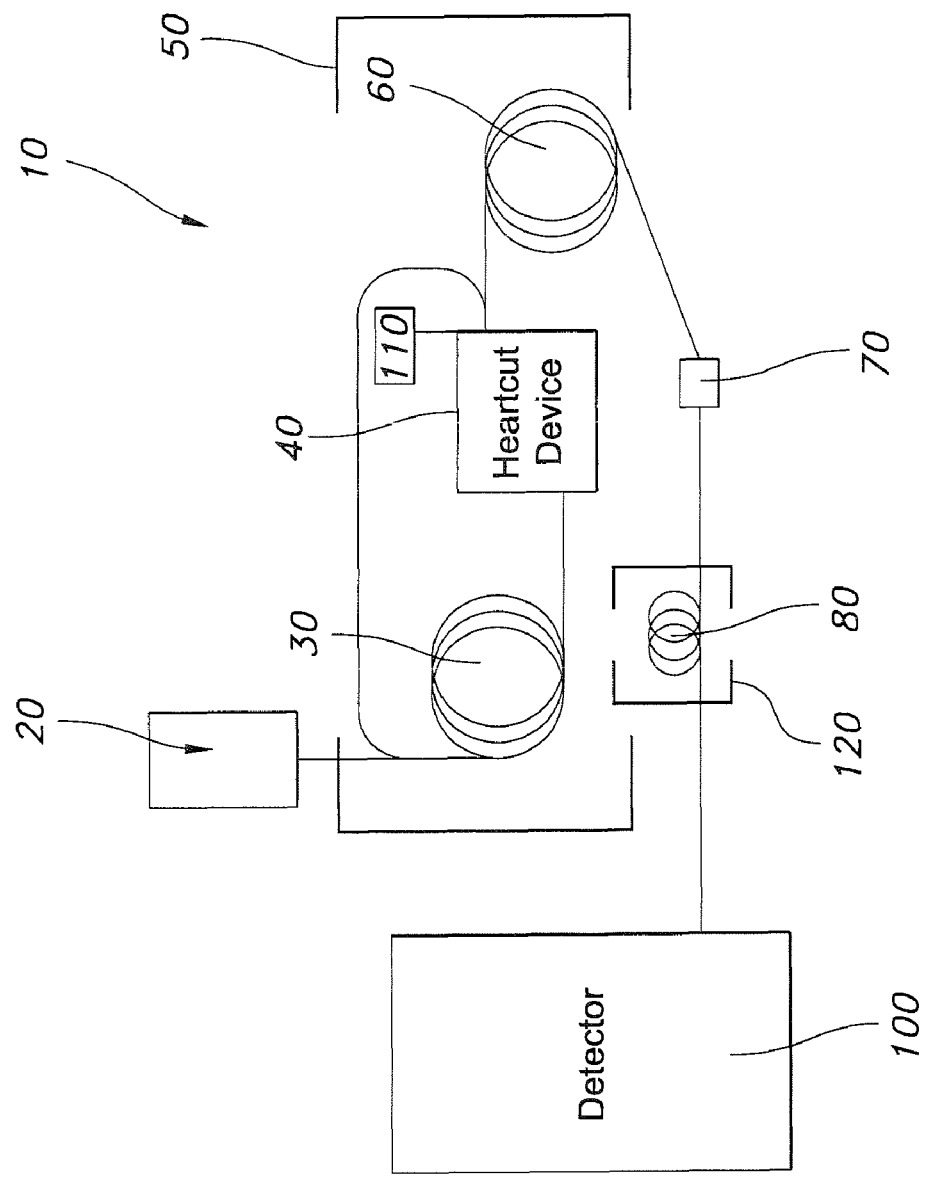
FIG. 3 is a schematic diagram illustrating one embodiment of the method of the present invention.

FIG. 3 illustrates another embodiment of the method of the present invention directed to a method for identifying the composition of a sample using chromatograph 10 as described in a manner as described relating to FIG. 1 that further comprises introducing at least one of the heartcut fractions onto first column 30 to further separate the fraction into at least two constituents. At least one of the constituents is then introduced into heartcut device 40 to further separate the constituent into at least two analytes. FIG. 3 illustrates an alternate embodiment where first column 30, heartcut device 40, and second column 60 are all within temperature control device 50. It will be appreciated by those skilled in the art that there are various ways chromatograph 10 may be configured.

Having described the invention in detail, those skilled in the art will appreciate that modifications of the invention may be made without departing from the spirit and scope thereof. Therefore, it is not intended that the scope of the invention be limited to the specific embodiments and examples described. Rather, it is intended that the appended claims and their equivalents determine the scope of the invention.

I claim:

1. A method for identifying the composition of a sample, comprising the steps of:
   introducing said sample onto a first column whereby said sample is separated into at least two segments;
   introducing said segments into a heartcut device whereby said at least two segments are selectively separated into at least two heartcut fractions;
   introducing at least one of said fractions onto a second column whereby said at least one fraction is further separated into at least two analytes;
   introducing at least one said analyte from said second column to a gas chromatography connector and thermal modulator;
   introducing said at least one analyte from said connector and modulator onto a third column;
   introducing said at least one analyte from said third column into a detector; and
   detecting said at least one analyte.

2. The method of claim 1 further comprising the step of:
   introducing said at least one analyte from said third column onto a fourth column, wherein said first column is operably coupled to said heartcut device, said heartcut device is operably coupled to said second column, said second column is operably connected to said connector, said connector is operably connected to said third column, and said third column is operably connected to said fourth column.

3. The method of claim 2 further comprising the step of:
   introducing said at least one analyte from said fourth column onto a fifth column, wherein said fourth column and said fifth column are operably connected.

4. The method of claim 1 wherein said sample is introduced onto said first column by an injecting device wherein said injecting device is selected from the group consisting of a split/splitless injector, an on-column inlet, a thermal desorption device, a PTV injector, a gas source inlet, a gas switching valve, a purge-and-trap system, and a solid phase microextraction.

5. The method of claim 1 wherein said step of introducing said sample onto a first column and said step of introducing said at least one segments into said heartcut device occur within a temperature controlling device.

6. The method of claim 5 wherein said temperature controlling device is selected from the group consisting of an oven and a heating jacket.

7. The method of claim 1 wherein said heartcut device is selected from the group consisting of a valve, a SGE heartcut device, a Dean's switch and a Gerstel heartcut device.

8. The method of claim 1 wherein said columns are selected from the group consisting of a packed column, a capillary column, a micropacked column, and a microfast column.

9. The method of claim 1 wherein said detector is selected from the group consisting of a flame ionization detector, a mass spectrometer, a thermal conductivity detector, a discharge ionization detector, an electron capture detector, a flame photometric detector, a Hall electrolytic conductivity detector, a helium ionization detector, a nitrogen phosphorus detector, a mass selective detector, a photo-ionization detector, and a pulsed discharge ionization detector.

10. The method of claim 1 wherein said third column is contained within a temperature controlling device.

11. A method for identifying the composition of a sample, comprising the steps of:
    introducing said sample onto a first column whereby said sample is separated into at least two segments;
    introducing said segments into a heartcut device whereby said segments are selectively separated into at least two heartcut fractions;
    introducing at least one of said fractions onto said first column whereby said heartcut fraction is further separated into at least two constituents;
    introducing at least one of said constituents into said heartcut device whereby said constituent is further separated into at least two analytes;
    introducing at least one of said at least one analytes onto a second column;
    introducing said at least one analyte from said second column to a gas chromatography connector and thermal modulator;
    introducing said at least one analyte from said connector and modulator onto a third column;
    introducing said at least one analyte from said third column into a detector; and
    detecting said at least one analyte.

12. A method for identifying the composition of a sample using multidimensional chromatography, comprising the steps of:
    introducing said sample onto a first column whereby said sample is separated into at least two segments;
    introducing said at least two segments into a heartcut device whereby said segments are selectively separated into at least two heartcut fractions and wherein said first column is operably coupled to said heartcut device, further wherein said first column and said heartcut device are in a first temperature controlling device wherein the temperature of said first temperature controlling device ranges from about 40° C. to about 320° C.;
    introducing at least one of said fractions onto a second column whereby said at least one fraction is further separated into at least two analytes and wherein said heartcut device is operably coupled to said second column, further wherein said second column is in said first temperature controlling device;
    introducing at least one said analyte from said second column to a gas chromatography connector and thermal modulator wherein said second column and said connector are operably coupled;
    introducing said at least two analyte from said connector onto a third column wherein said connector and modulator and said third column are operably coupled and wherein said third column is within a second temperature controlling device;
    introducing said at least two analyte from said third column into a detector wherein said third column and said detector are operably coupled; and
    detecting said at least one analyte.

13. A multidimensional chromatograph comprising:
    an introduction device;
    a first column wherein said introduction device introduces a sample onto said first column whereby said sample is separated into at least two segments;
    a heartcut device wherein said at least two segments are introduced to said heartcut device and whereby said at least two segments are selectively separated into at least two heartcut fractions;
    a second column wherein at least one of said fractions is introduced and further separated into at least two analytes;
    a gas chromatography connector and thermal modulator wherein at least one of said analytes is introduced;
    a third column wherein said analyte is introduced; and
    a detector wherein said analyte is introduced and identified.

14. The chromatograph of claim 13 wherein said columns are selected from the group consisting of a packed column, a capillary column, a micropacked column, and a microfast column.

15. The chromatograph of claim 13 wherein said first column is a capillary column with a size of about 30 m×0.25 mmID×1 μm df, said second column is a capillary column with a size of about 30 m×0.25 mmID×1 μm df, and said third column is a capillary column with a size of about 1 m×0.10 mmID×0.1 μm df.

16. The chromatograph of claim 13 wherein said introduction device is selected from the group consisting of a split/splitless injector, an on-column inlet, a thermal desorption device, a PTV injector, a gas source inlet, a gas switching valve, a purge-and-trap system, and a solid phase microextraction.

17. The chromatograph of claim 13 wherein said first column and said heartcut device are within a temperature controlling device.

18. The chromatograph of claim 13 wherein said heartcut device is selected from the group consisting of a valve, a SGE heartcut device, a Dean's switch and a Gerstel heartcut device.

19. The chromatograph of claim 13 wherein said detector is selected from the group consisting of a flame ionization detector, a mass spectrometer, a thermal conductivity detector, a discharge ionization detector, an electron capture detector, a flame photometric detector, a Hall electrolytic conductivity detector, a helium ionization detector, a nitrogen phosphorus detector, a mass selective detector, a photo-ionization detector, and a pulsed discharge ionization detector.

* * * * *